(12) United States Patent
Takino

(10) Patent No.: US 9,980,860 B2
(45) Date of Patent: May 29, 2018

(54) PULL-ON WEARING ARTICLE

(71) Applicant: UNICHARM CORPORATION, Shikokuchuo-shi, Ehime (JP)

(72) Inventor: Shunsuke Takino, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 80 days.

(21) Appl. No.: 14/424,021

(22) PCT Filed: Aug. 19, 2013

(86) PCT No.: PCT/JP2013/072070
§ 371 (c)(1),
(2) Date: Feb. 25, 2015

(87) PCT Pub. No.: WO2014/034459
PCT Pub. Date: Mar. 6, 2014

(65) Prior Publication Data
US 2015/0182389 A1    Jul. 2, 2015

(30) Foreign Application Priority Data
Aug. 31, 2012  (JP) ................... 2012-192682

(51) Int. Cl.
*A61F 13/15* (2006.01)
*A61F 13/56* (2006.01)
(Continued)

(52) U.S. Cl.
CPC ...... *A61F 13/565* (2013.01); *A61F 13/15756* (2013.01); *A61F 13/496* (2013.01);
(Continued)

(58) Field of Classification Search
CPC .............. A61F 13/565; A61F 13/49012; A61F 13/622; A61F 13/15756
See application file for complete search history.

(56) References Cited

U.S. PATENT DOCUMENTS

| 5,624,428 A | 4/1997 | Sauer |
| 2005/0038405 A1* | 2/2005 | Shimoe ............ A61F 13/58 |
| | | 604/389 |

(Continued)

FOREIGN PATENT DOCUMENTS

| JP | 6-77719 U | 11/1994 |
| JP | 2003-290287 A | 10/2003 |

(Continued)

OTHER PUBLICATIONS

International Search Report dated Oct. 15, 2013 in International Application No. PCT/JP2013/072070.
(Continued)

*Primary Examiner* — Todd J Scherbel
*Assistant Examiner* — Sara Sass
(74) *Attorney, Agent, or Firm* — HAUPTMAN HAM, LLP

(57) ABSTRACT

A pull-on wearing article includes first and second waist regions, and tape fasteners. The first waist region includes elasticity in the lateral direction. The tape fasteners include a fixed section fixed in the vicinity of a lateral region and a free section that includes a fastening section in which the tape fastener is removable with respect to the outer surface of the second waist region. The free section includes a holding end and a holding section extended from the fastening section to an outer side in the lateral direction, and the holding end is releasably fixed on a non-skin facing surface in the vicinity of the lateral edge of the first waist region, and a region between the fastening section of the first waist region and the holding end contracts, whereby the holding section assumes a convexly curved shape.

16 Claims, 10 Drawing Sheets

(51) Int. Cl.
   *A61F 13/496*   (2006.01)
   *A61F 13/551*   (2006.01)
   *A61F 13/49*    (2006.01)
   *A61F 13/62*    (2006.01)

(52) U.S. Cl.
   CPC .... *A61F 13/49012* (2013.01); *A61F 13/5512* (2013.01); *A61F 13/622* (2013.01)

(56) References Cited

U.S. PATENT DOCUMENTS

| | | | |
|---|---|---|---|
| 2005/0070868 A1* | 3/2005 | Ito | A61F 13/493 604/385.01 |
| 2005/0090788 A1* | 4/2005 | Shimada | A61F 13/496 604/367 |
| 2005/0131378 A1 | 6/2005 | Sasaki et al. | |

FOREIGN PATENT DOCUMENTS

| | | |
|---|---|---|
| JP | 2004-141641 A | 5/2004 |
| JP | 2005-124871 A | 5/2005 |
| JP | 2007-222256 A | 9/2007 |
| WO | 95/29657 A1 | 11/1995 |

OTHER PUBLICATIONS

Extended European Search Report in EP Application No. 13833075.8, dated Apr. 14, 2016.

* cited by examiner

PULL-ON WEARING ARTICLE

RELATED APPLICATIONS

The present application is a National Phase of International Application Number PCT/JP2013/072070, filed Aug. 19, 2013, and claims priority of Japanese Patent Application No. 2012-192682 filed on Aug. 31, 2012.

TECHNICAL FIELD

The present invention relates to a pull-on wearing article, more particularly, relates to a pull-on wearing article such as a disposable pants-type diaper having tape fasteners and a disposable toilet training pant.

BACKGROUND

Conventionally, pull-on disposable wearing articles having tape fasteners have been known. For example, Patent Literature 1 discloses a pull-on disposable wearing article in which a plurality of waist elastics are disposed in rear and front waist regions, and a pair of tape fasteners are fixed on a series of seams that join the rear and front waist regions with each other.

CITATION LIST

Patent Literature

{PTL 1} JP 1994-77719 U

SUMMARY

Technical Problem

According to the wearing article disclosed in Patent Literature 1, when the wearing article is worn, a waist-cross size is adjusted by using the tape fasteners, so that the wearing article can be fitted to wearers of various sizes and can be prevented from being slid down, and after the use of the wearing article, the wearing article is rolled up in such a manner as to wrap body exudates, and a state where the wearing article is rolled up with the tape fasteners is maintained so that the wearing article may be hygienically disposed of.

However, for the above-mentioned wearing article, waist elastics secured in an stretched state in a series of side seams of the article are contracted in the waist-cross direction, so that a fixed section of the tape fastener is contracted in response to the waist elastics, whereas a free end portion of the tape fastener is not fixed in a waist region, and the free end portion may be spaced away from the waist region curved along the body of a wearer, and the free end protrudes or floats to the outside of the waist region. Normally, the tape fasteners are formed of a plastic sheet having high stiffness in order to prevent deformation and rupture during operations, compared with sheet material that form the waist region, so that the contact of the wearer body with the free end portion protruded in the above-mentioned manner might cause an unpleasant irritation. When the entire free end portion is temporally tacked in order to prevent the above-mentioned problem, it is difficult to hold the tip end of the free end portion when the tape fasteners are extended.

An object of the present invention is to provide an improved pull-on wearing article that includes tape fasteners that do not cause irritation, even when the tape fasteners contact the skin of a wearer, and that can be stably hooked and provides easy operation.

Solution to Problem

According to the present invention, there is provided a pull-on wearing article having a longitudinal direction, a lateral direction, and including a non-skin facing surface, a skin facing surface opposed to the non-skin facing surface, a first waist region that is one of rear and front waist regions, a second waist region that is a remainder of the rear and front waist regions, and a crotch region between the first and second waist regions, wherein longitudinal extending lateral edge portions of the first and second waist regions are joined with each other, and tape fasteners are mounted on the non-skin facing surface in a lateral region of the first waist region.

The pull-on wearing article further includes at least the first waist region of the first and second waist regions is elastically stretchable in the lateral direction. The tape fastener includes a fixed section fixed on the lateral region of the first waist region, a free section formed with a fastening section that is releasably fastened to the non-skin facing surface in the second waist region. The free section includes a holding section extending from the fastening section to an outer side in the lateral direction and a holding end releasably fixed on the non-skin facing surface in the lateral region of the first waist region. A region between the fastening section of the first waist region and the holding end contracts, whereby the holding section assumes a convexly curved shape.

Advantageous Effects of Invention

According to one or more embodiments of the pull-on wearing article of the present invention, the tape fasteners are mounted on the lateral region of the first waist region, and the holding section in the free section of the tape fastener assumes a convexly curved shape under the contraction of the first waist region in the direction that the holding section is spaced away from the outer surface of the first waist region, so that a wearer or a helper of the wearer can easily hold the holding section, which provides easy operation. Also, the contraction of the first waist region provides the fixed section with an undulated shape, and a force that pulls the free section backward is acted in a state where the free section is adhered to the second waist region, so that the tape fasteners are more stably mounted. Furthermore, the tape fasteners are formed of relatively flexible materials to the extent that the fixed section undulates under the contraction of the first waist region, so that the tape fasteners do not cause irritation, even when the end edge of the free section contacts the skin of a wearer.

BRIEF DESCRIPTION OF DRAWINGS

The drawings illustrate specific embodiments of the present invention including optional and preferred embodiments as well as essential features of the invention.

DESCRIPTION OF EMBODIMENTS

First Embodiment

Figure 1:
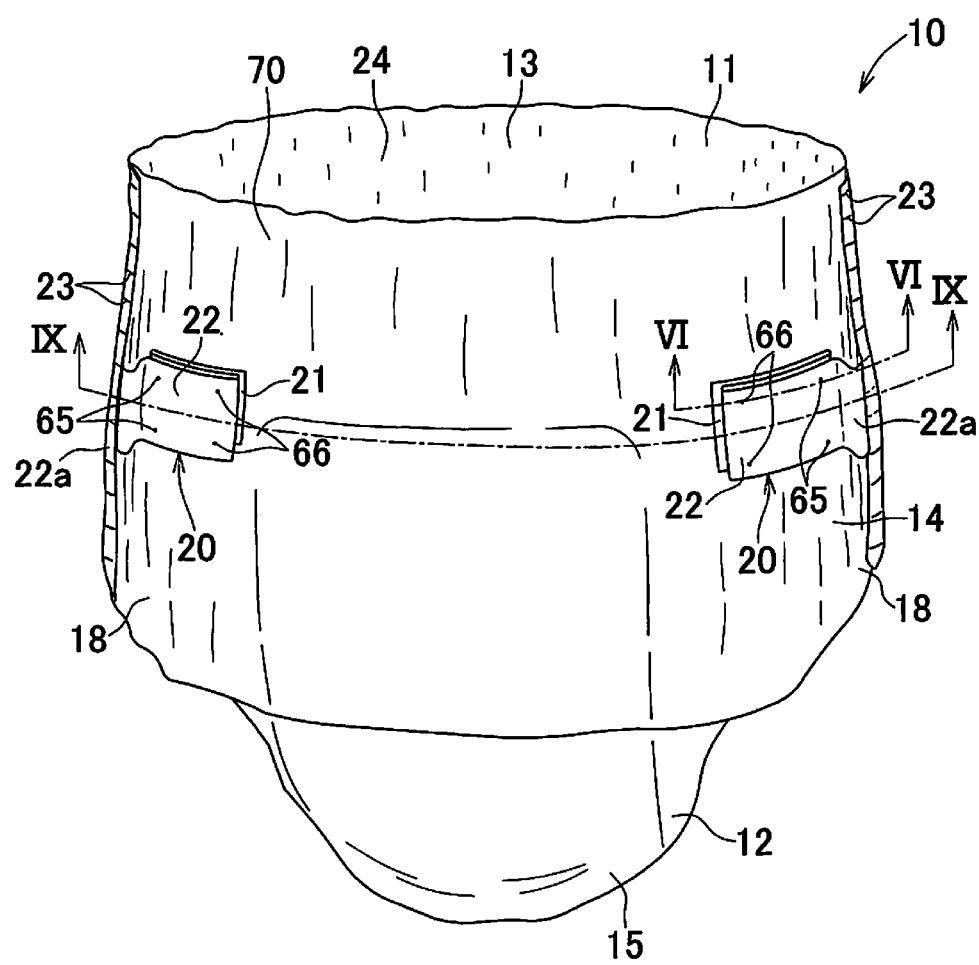
FIG. 1 is a perspective view of a disposable diaper viewed from a rear side, which is shown as one example of a pull-on wearing article according to a first embodiment of the present invention.

Referring to FIGS. 1 to 4, a disposable diaper 10, shown as one example of a pull-on wearing article of the present invention, includes a longitudinal direction Y parallel to a longitudinal axis P, a lateral direction X parallel to a lateral axis Q, a skin facing surface, and a non-skin facing surface opposing to the skin facing surface.

The diaper 10 includes an annular elastic waist panel 11 extending in the waist-cross direction and a liquid absorbent structure 12 joined with the elastic waist panel 11, and includes a front waist region (one of a first or second waist region) 13, a rear waist region (a remainder of the first or second waist region) 14, and a crotch region 15 positioned between the front waist region 13 and the rear waist region 14. The diaper 10 is symmetrically formed with respect to the longitudinal axis P, and the elastic waist panel 11 includes a front waist panel 16 lying in the front waist region 13, a rear waist panel 17 lying in the rear waist region 14, and tape fasteners 20 coupled with respective lateral regions 18 of the rear waist panel 17.

The front waist region 13 has a laterally long rectangular shape contoured by an inner end edge 13a and an outer end edge 13b extending in the lateral direction X, and lateral edges 13c and 13d extending in the longitudinal direction Y.

The rear waist region 14 is contoured by an inner end edge 14a extending and an outer end edge 14b extending in the lateral direction X, respectively, lateral edges 14c, 14d extending in the longitudinal direction Y, and curved corner edges 14e, 14f that connect the inner end edge 14a with the lateral edges 14c, and the rear waist region 14 has an approximately trapezoidal shape protruding toward lateral center line Q-Q. The lateral edges 13c, 13d of the front waist region 13 are respectively overlapped with the lateral edges 14c, 14d of the rear waist region 14, and the lateral edges 13c, 13d and the lateral edges 14c, 14d are joined by a series of side seams 23 continually extending in the longitudinal direction Y, whereby a waist opening 24 and a pair of leg openings are defined. The side seams 23 are made by a known join means, for example, various thermal welding means such as heat embossing/debossing and ultrasonic machining.

The tape fastener 20 includes a first end (an holding end) 20a and a second end (a fixed end) 20b, both of which oppose to each other in the lengthwise direction thereof, a fixed section 21 fixed in the lateral region 18 of the rear waist region 14, and a free section 22 continuously extending from the fixed section 21. While the fixed section 21 is fixed on the external surface of the lateral region 18 of the rear waist panel 17, the holding end 20a is releasably adhered to the lateral region 18 of the rear waist panel 17.

In this embodiment, the tape fasteners 20 are mounted in the lateral regions 18 of the rear waist region 14. However, the mounting portions of the tape fasteners 20 may be placed on one lateral region 18 or the lateral regions of the front waist region 13 as long as the later-mentioned advantageous effects of the present invention are achieved.

Figure 3:
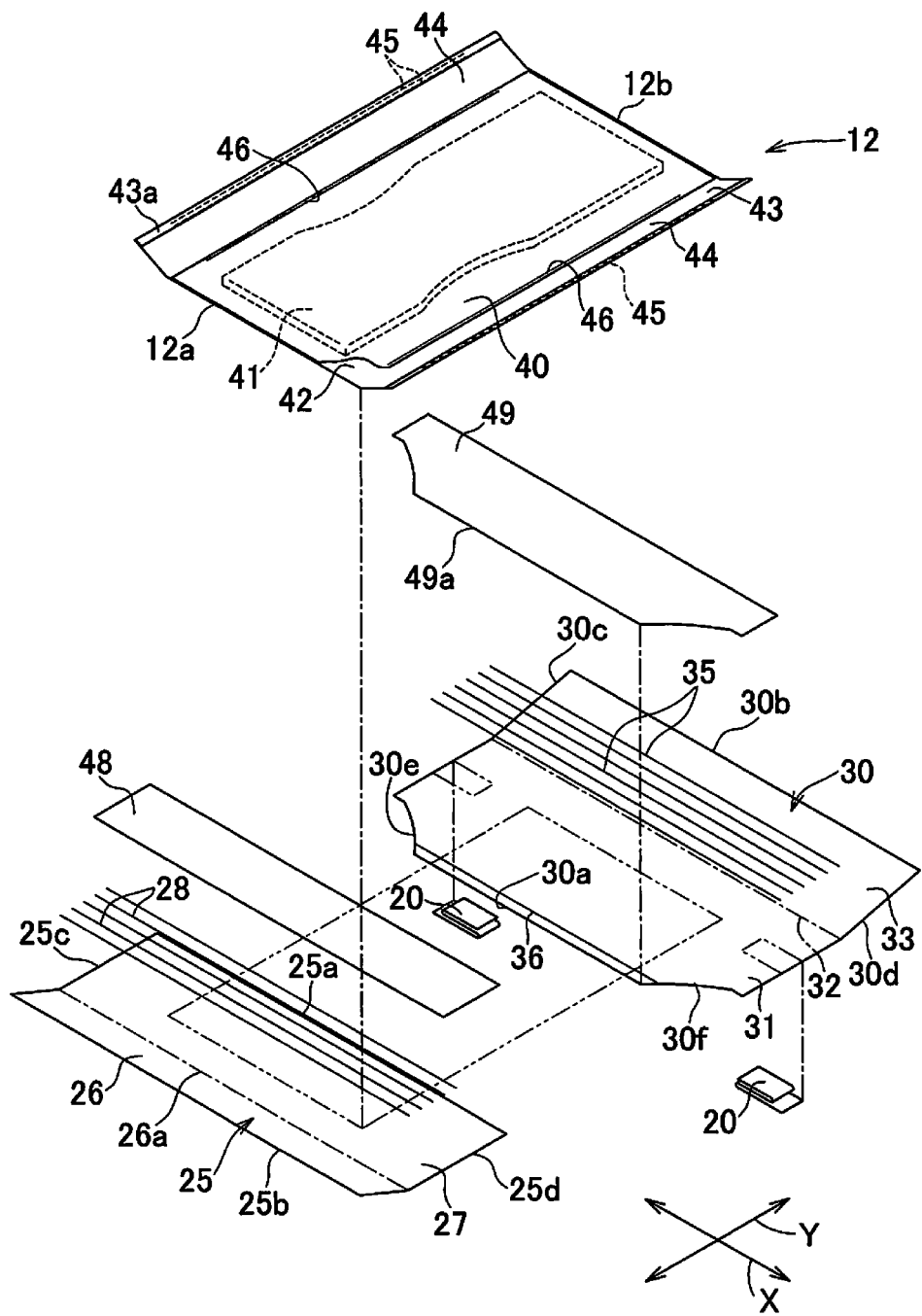
Figure 4:
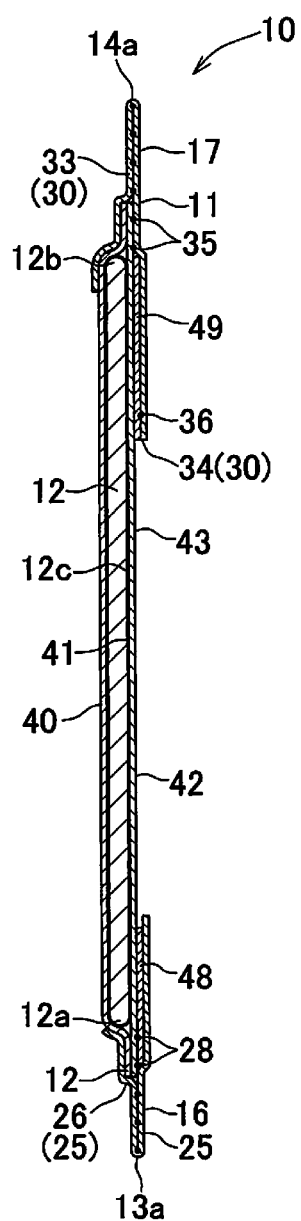
FIG. 4 is a schematic cross-sectional view taken along line IV-IV of FIG. 2.

In particular, referring to FIG. 3, the front waist panel 16 includes a rectangular front waist sheet 25 that forms the front waist region 13. The front waist sheet 25 is contoured by an inner end edge 25a and an outer end edge 25b extending in the lateral direction X, respectively, and spaced apart from and opposed to each other in the longitudinal direction Y, and lateral edges 25c, 25d extending in the longitudinal direction Y. The front waist sheet 25 includes a fold section 26 extending in the longitudinal along the front end portion 12a of the liquid absorbent structure 12, and the fold section 26 is folded on the inner surface of the front waist region 25 in the longitudinal direction Y along a fold line 26a extending in the lateral direction X and fixed on a later-mentioned front elastic sheet 48 and the liquid absorbent structure 12. A plurality of thread-, strand- or string-like front waist elastics 28 are contractibly secured in a stretched state in the lateral direction X between a main section 27 of the front waist sheet 25 and the fold section 26, and between the main section 27 and the front end portion 12a of the liquid absorbent structure 12. The front waist panel 16 further includes the front elastic sheet 48 that is stretchable at least in the lateral direction X and disposed on the inner surface of the main section 27 of the front waist sheet 25. The front waist region 13 is elasticized as a whole in the lateral direction X with the front waist elastics 28 and the front elastic sheet 48.

The rear waist panel 17 includes a rear waist sheet 30 having an approximately trapezoidal shape, which forms the rear waist region 14. The rear waist sheet 30 is contoured by an inner end edge 30a and an outer end edge 30b extending in the lateral direction X, respectively and spaced apart from and opposed to each other in the longitudinal direction Y, lateral edges 30c, 30d extending in the longitudinal direction Y, and curved corner edges 30e, 30f that connect the lateral edges 30c, 30d with the inner end edge 30a. The rear waist sheet 30 includes a main section 31, a fold line 32 extending in the lateral direction X along the rear end portion 12b of the liquid absorbent structure 12 between the lateral edges 30c, 30d, and a fold section 33 is folded on the inner surface in the longitudinal direction Y along the fold line 32 and fixed on the inner surface of the rear end portion 12b of the liquid absorbent structure 12 and the inner surface of the main section 31. A plurality of thread-, strand- or string-like waist elastics 35 are contractibly secured in a stretched state in the lateral direction X between the main section 31 of the rear waist sheet 30 and the fold section 33 and the rear end portion 12b of the liquid absorbent structure 12. The rear waist panel 17 further includes a rear elastic sheet 49, which is disposed on the inner surface of the main section 31 in such a manner that the end edge 49a and lateral edges of the rear elastic sheet 49 respectively align with the inner end edge 30a of the rear waist sheet 30, the curved corner edges 30e, 30f and parts of the lateral edges 30c, 30d. Thread-, strand- or string-like buttocks elastics 36 extending in the lateral direction X are contractibly secured in a stretched state along the lateral inner end edge 30a between the rear waist sheet 30 and the rear elastic sheet 49. The rear waist region 14 is elasticized as a whole in the lateral direction X with the rear waist elastics 35, the rear elastic sheet 49, and the buttocks elastics 36.

The front waist sheet 25 and the rear waist sheet 30 may be formed, for example, of fibrous nonwoven fabrics, whose basis mass ranges from about 10 to about 40 g/m2, and whose fiber density ranges from about 0.03 to about 0.1 g/cm3, such as spunbonded nonwoven fabrics, SMS (spunbonded/meltblown/spunbonded) fibrous nonwoven fabrics, air through fibrous nonwoven fabrics, plastic sheets, and laminate sheets of these fibrous nonwoven fabrics. For example, thread-, strand- or string-like elastic materials having fineness ranging from about 300 to 500 dtex and these stretch magnification ranging from about 1.5 to 3.5 times, can be used to the front waist elastics 28, the rear waist elastics 35, and the buttocks elastics 36. However, the fineness and the stretch magnification can be appropriately changed. It is preferable that the front waist elastics 28, the rear waist elastics 35, and the buttocks elastics 36 be fixed through hot melt adhesives partially applied at least in the lateral direction X because the front waist region 13 and the rear waist region 14 contract in the lateral direction X. For example, elastic fibrous nonwoven fabrics made of elastomer fabrics, whose basis mass ranges from about 20 to about 40 g/m2, and whose fiber density ranges from about 0.01 to about 0.04 g/cm3, can be used to the front elastic sheet 48 and the rear elastic sheet 49. The front elastic sheet 48 and the rear elastic sheet 49 are respectively fixed on the front waist sheet 25 and the rear waist sheet 30 in a state where the sizes of the front elastic sheet 48 and the rear elastic sheet 49 are stretched in the lateral direction X about 2.4 times longer than those in their unstretched states.

The liquid absorbent structure 12 is formed in an approximately rectangular shape and has the front end portion 12a, the rear end portion 12b, and a center portion 12c between the front end portion 12a and the rear end portion 12b. The liquid absorbent structure 12 includes a bodyside liner 40 disposed on the skin facing surface side and formed of fibrous nonwoven fabrics having liquid permeable property, an absorbent core 41 having a curved lateral edge, a liquid impermeable leakage-barrier sheet 42 covering the entire bottom surface of the absorbent body 41, and a hydrophobic cover sheet 43 that forms the whole of the non-skin facing surface of the liquid absorbent structure 12. The absorbent body 41 includes a core formed of a mixture of fluff pulp and superabsorbent polymer particles, and a liquid absorbent and diffusible sheet such as tissue paper, wrapping the core entirely.

The cover sheet 43 includes lateral edge portions 44 extending outward from the lateral edges of the leakage-barrier sheet 42. The lateral edge portions 44 has sleeve-shaped free edge portions 43a are folded inward along the lateral edges of the leakage-barrier sheet 42 and fixed on the bodyside surface of the bodyside liner 40 except the free edge portions 43a. A plurality of thread-, strand- or string-like elastics 45 extending in the longitudinal direction Y are contractibly secured in a stretched state within the free edge portions 43a. The contraction of the elastics 45 allows the free edge portions 43a to space away from the bodyside liner 40 to the bodyside of the wearer, so that the free edge portions 43a can be fitted to the thighs of the wearer, and the leakage of the body exudates can be prevented. Also, a plurality of thread-, strand- or string-like leg elastics 46 are contractibly secured between the lateral edge portions 44 of the cover sheet 43 and the leakage-barrier sheet 42.

Figure 2:
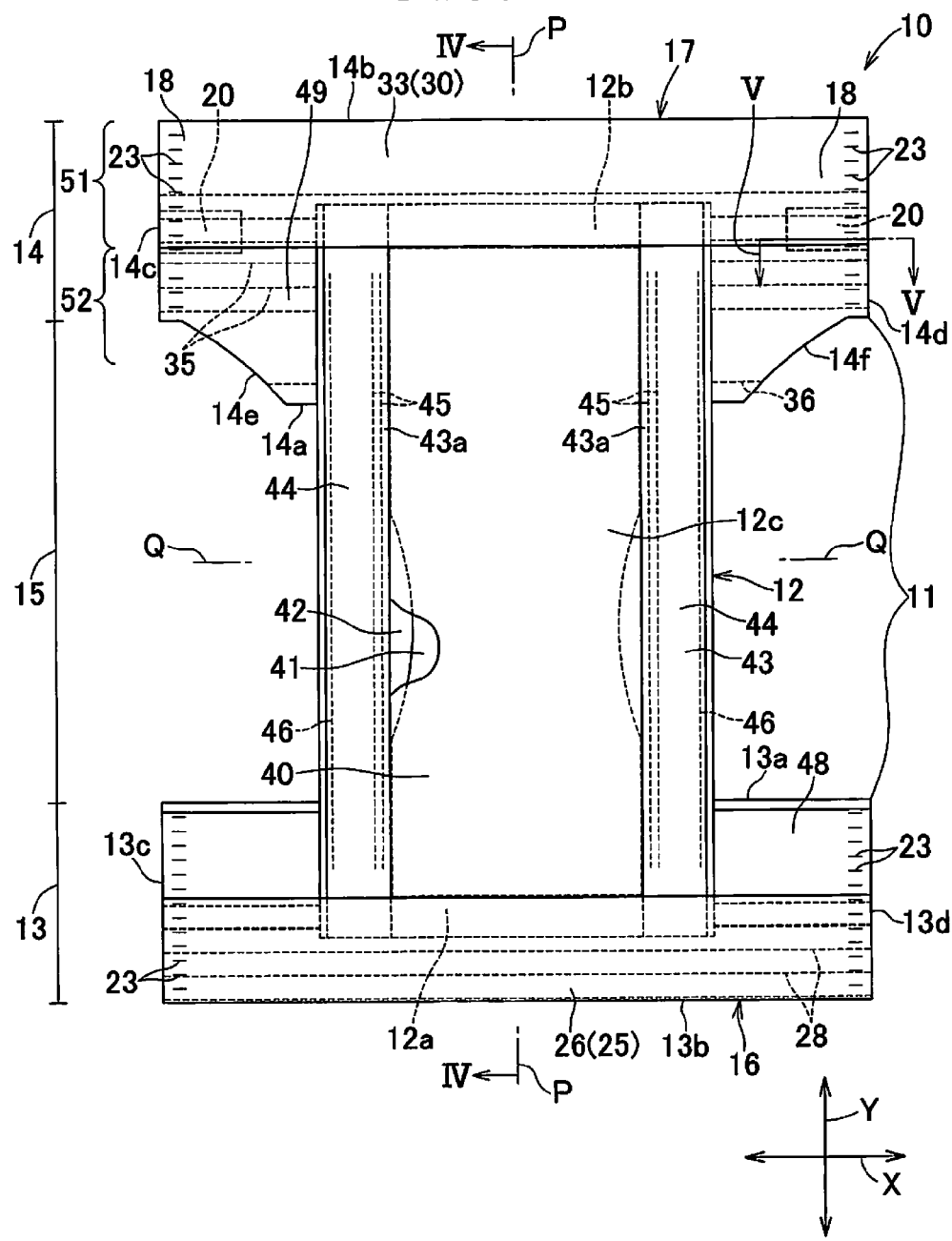
FIG. 2 is a partially broken opened plan view of the diaper viewed from an inner side of the diaper in a state where a FIG. 3 is an exploded perspective view of the diaper.

Referring to FIG. 2, the rear waist region 14 is formed with a first elastic region 51 that is elasticized at least in the lateral direction X with the rear waist elastics 35, and a second elastic region 52 elasticized at least in the lateral direction X with at least the rear elastic sheet 49. The fixed section 21 (see FIG. 1) of the tape fastener 20 is positioned in the first elastic region 51 of the lateral region 18 of the rear waist region 14, and forms undulations by a contractive force generated during the contraction of the first elastic region 51, as will be described later in more detail. For the first elastic region 51 and the second elastic region 52, it is preferable that the tensile stress per unit area with respect to one of the first elastic region 51 and the second elastic region 52 be higher than that of the other, in particular, the tensile stress per unit area with respect to the latter second elastic region 52 be higher than that of the former first elastic region 51, in order to fit the diaper 10 to the wearer without pressing the abdominal region of the wearer and prevent the diaper 10 from being slipped down when worn.

Figure 5:
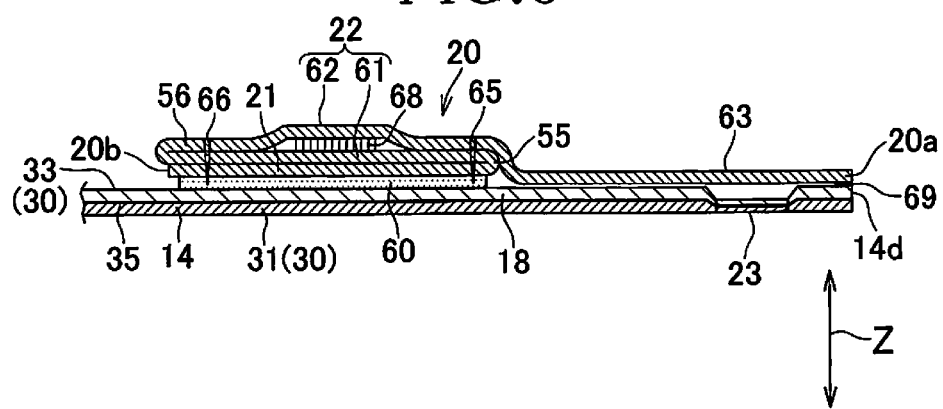
FIG. 5 is a schematic cross-sectional view taken along line V-V of FIG. 2.

Referring to FIG. 5, this shows the tape fasteners 20 in a state where the rear waist region 14 is expanded in response to the contraction in the elastic region of the rear waist region 14 in the longitudinal direction Y and the lateral direction X, to the extent that creases are not formed on the outer surface of the rear waist region 14. The pair of tape fasteners 20, which are fixed through a join section 60 on the outer surface of the lateral regions 18 of the rear waist region 14, are formed of continuous tape materials, which are folded in a roughly U-shaped cross section. The free section 22 of the tape fastener 20 includes a first free section 61 that is contiguous to the fixed section 21 and opposed to the fixed section 21 in the thickness direction Z of the tape fastener 20, and a second free section 62 that is contiguous to the first free section 61 and opposed to the first free section 61 in the thickness direction Z. In the folded state of the free section 22, the fixed section 21, the first free section 61, and the second free section 62 are temporarily tacked by tack portions 65, 66 at first and second folds 55, 56. The free section 22 further includes a holding section 63 extending outward in the lateral direction X from the tack portion 65 at the first fold 55. A fastening section 68 formed of hooking elements of mechanical fasteners or adhesives is disposed on the inner surface of the second free section 62 between the tack portions 65, 66. Preferably, an object to be fastened is formed of fibrous nonwoven fabrics. The holding end 20a of the tape fastener 20 has an inner surface thereof provided with an adhesive section 69 and is releasably adhered through the adhesive sections 69 onto the adjacent area inclusive of the lateral edge 14d positioned outboard of the side seams 23 in the lateral direction X.

The tape fastener 20 may be formed of fibrous nonwoven fabrics, for example, spunbonded fibrous nonwoven fabrics formed from heat fusible synthetic fibers such as polyethylene, polypropylene, polystyrene and having a basis mass ranging from about 30 to about 100 g/m2, preferably, from about 50 to about 80 g/m2. As will be described later in more detail, aside from the use of various known adhesive means such as hot melt adhesives as the adhesive section 69, which is used to fix the holding end 20a of the tape fastener 20 on the adjacent area inclusive of the lateral edge 14d, the holding end 20a of the tape fastener 20 can be thermally welded to the fibrous nonwoven fabric that forms the lateral edge 14d through the use of heat generated by a cutting means such as a cutter during manufacture of the diaper 10.

For example, the hot melt adhesives having a basis mass ranging from about 5 to about 20 g/m2 may be used for a join section 60. The tack portions 65, 66 may be created by applying known pressurization treatment or known pressurization heating treatment to portions to be tacked and can be created, for example, through the embossing/debossing treatment or ultrasonic treatment. When the pressurization heating treatment is applied, temporal tacking can be stably performed by thermal welding because the tape fastener 20 itself contains thermoplastic synthetic fibers.

Figure 6:
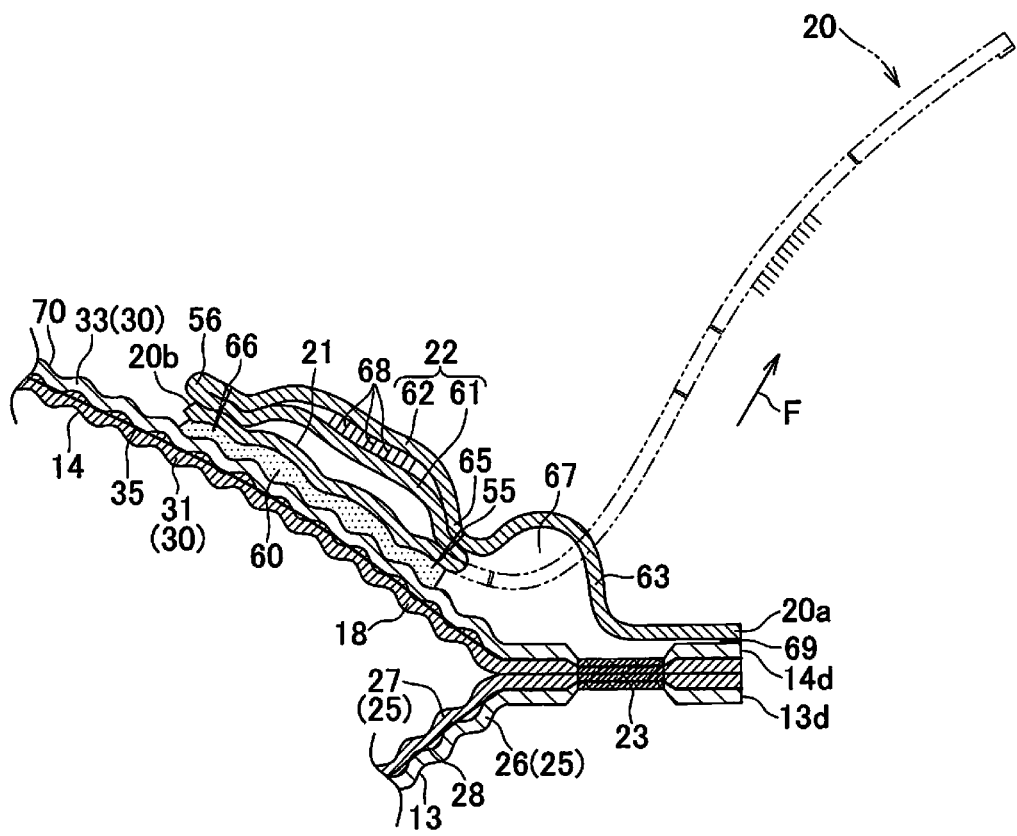
FIG. 6 is a schematic cross-sectional view taken along line VI-VI of FIG. 1.

Referring to FIG. 6, this shows a cross-sectional view taken line VI-VI of FIG. 1, wherein the whole of the rear waist region 14 is contracted in the lateral direction X with the rear waist elastics 35 when the diaper 10 is put on a wearer or when the diaper 10 is not put on the wearer. Accordingly, a plurality of gathers 70 continuously arranged in the lateral direction X are formed in the first elastic region 51 (see FIG. 2) where the rear waist elastics 35 of the rear waist region 14 are disposed.

Also, in a region where the fixed section 21 of the tape fastener 20 is disposed in the rear waist region 14, the fixed section 21 is continuously formed in the lateral direction under a contractive force of the rear waist elastics 35, whereby an undulation having less concaves and convexes than those of the gathers 70 is formed.

In the above-mentioned state, the first free section 61 of the free section 22 and the second free section 62, on which the first free section 61 is placed, are spaced away from the fixed section 21 between the tack portions 65, 66. Consequently, in the holding section 63, the size of the holding section 63 in terms of the length of a straight line ranging from the fixed end 20b of the fixed section 21 to the side seams 23 is smaller than the size of the holding section 63 before the first and second free sections 61, 62 are spaced away from the fixed section 21, and the holding section 63 is convexly spaced away from in the direction that the holding section 63 is spaced away from the lateral regions 18, that is, in the thickness direction of the lateral regions 18. Also, the fixed section 21 contracts with the rear waist region 14 and conforms to the body shape of the wearer, so that the holding section 63 consumes a shape that the holding section 63 is spaced further apart from the rear waist region 14. The holding section 63 is spaced away from the lateral regions 18 of the rear waist region 14, thereby defining a space 67 opened in the longitudinal direction Y therebetween. As described above, the rear waist elastics 35 are positioned in a region where the tape fastener 20 is disposed, the holding section 63 is spaced away from the lateral regions 18 of the rear waist region 14 in almost the entire width of the holding section 63, so that the whole of the holding section 63 convexly curved can be easily picked and pulled.

Thus, the holding section 63 is spaced away from the lateral regions 18 of the rear waist region 14 with being convexly curved, so that when the tape fasteners 20 are extended, the holding section 63 can be easily held, which provides easy operation, compared with when the holding section 63 is not spaced apart from the lateral regions 18. Unlike the present embodiment, in a state where the rear waist region 14 contracts, when the whole of the holding section 63 inclusive of the holding end 20a is not adhered to the lateral regions 18, the holding end 20a of the holding section 63 might extend to outboard of the lateral edge 14d or float from the lateral regions 18, and the holding end 20a might contact and irritate the skin of a wearer or a helper of the wearer during operation of wearing.

However, according to the tape fasteners 20 of this embodiment, as described above, the holding section 63 assumes the shape convexly curved on the lateral regions 18 of the rear waist region 14, so that the wearer or the helper of the wearer can pick and pull up the convexly curved holding section 63 with the fingers, and the tape fasteners 20 can be easily extended. Also, the holding end 20a is adhered with the adhesive section 69, there is no likelihood that the holding end 20a might contact and irritate the skin of the wearer. Furthermore, the tape fasteners 20 are formed of fibrous nonwoven fabrics, which are relatively flexible materials, so that the holding section 63 can assume the shape convexly curved under the contractive action of the rear waist elastics 35 of the rear waist region 14, and there is no likelihood that the holding end 20a might cause severe irritation, even when the adhesive section 69 is unexpectedly released, and the holding end 20a contacts the skin of the wearer or the helper of the wearer, compared with when the holding end 20a is formed of plastic sheets having relatively high stiffness. However, the tape fasteners 20 need not be necessarily formed of fibrous nonwoven fabrics as an optimum, but other appropriate materials having approximately the same stiffness as that of the fibrous nonwoven fabrics, for example, materials, which are made of paper materials or plastic materials and formed into the tape, may be used.

Also, when the first free section 61 and the second free section 62 are temporarily tacked to each other at positions different from the above-mentioned position, it is empirically necessary to turn up the holding section 63 inward in the rear waist region 14 once, in a state where the holding section 63 is picked, and subsequently perform the operation (two steps) of pulling up the holding section 63 outward, in order to release the entire temporal tacking. In this embodiment, the fixed section 21, the first free section 61, and the second free section 62 are temporarily tacked together by the same tack portions 65, 66, and after the holding section 63 is picked, and the holding end 20a is peeled off from the adjacent area inclusive of the lateral edge 14d, the tack portions 65, 66 are all released, for example, by pulling the holding section 63 in the direction of an arrow F, so that the tape fastener 20 can be extended in one operation (one step).

Figure 7:
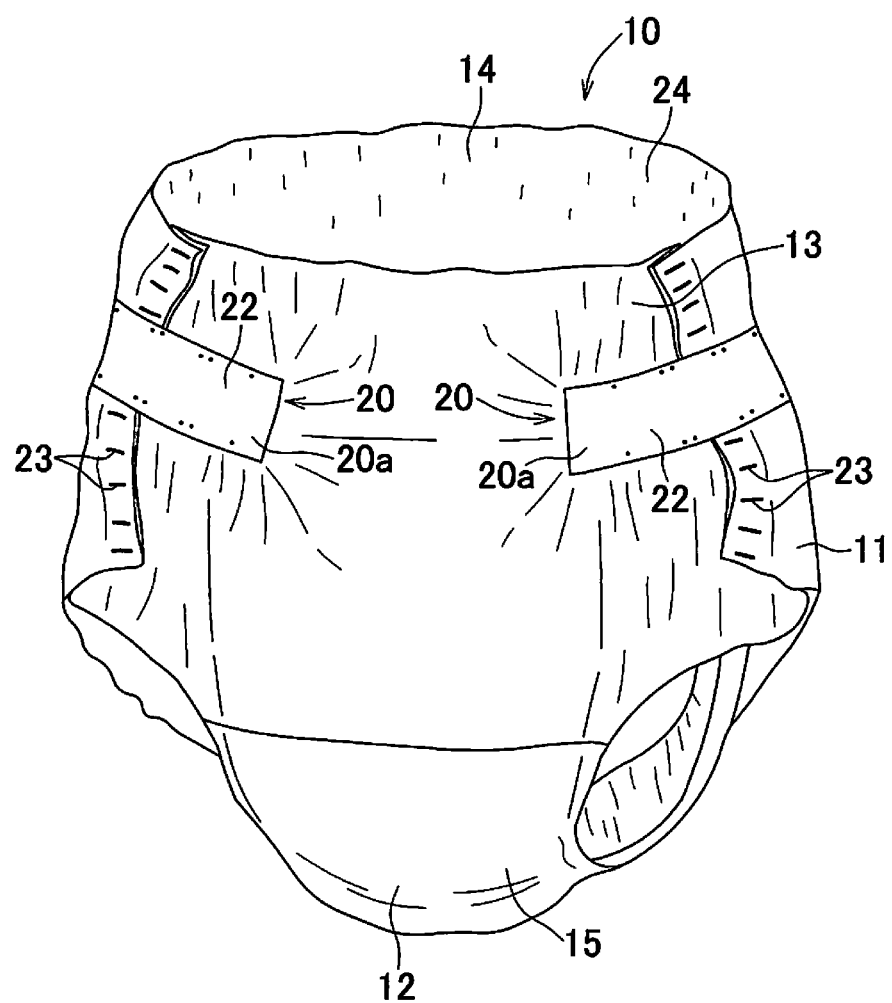
FIG. 7 is a perspective view of the diaper viewed from the front side, which shows the state of use regarding tape fasteners.

Referring to FIG. 7, the holding section 63 is picked and pulled up, and the tape fastener 20 is extended, and the free section 22 is releasably fastened on the outer surface of the front waist region 13 through the fastening section 68, so that a section about the waist surrounding of the front waist region 13 and the rear waist region 14 can be tightened, and even when the size about the wearer's waist is varied, the size about the waist surrounding may be easily adjusted accordingly. Also, when the front elastic sheet 48 and the rear elastic sheet 49 are disposed on the inner surface of the diaper 10, and the size of the waist region is reduced by adjustment of the tape fastener 20 and fitted to the body of a baby, whose navel portion and its vicinity are relatively soft, an oppressive feeling can appropriately be suppressed.

Also, when the tape fastener 20 is formed of plastic sheets having relatively high stiffness, it is hard to curve the tape fastener 20 along the outer surface of the front waist region 13, and it might be difficult to fit the whole of the front waist region 13 to the body of the wearer. When the tape fastener 20 is formed of fibrous nonwoven fabrics or sheet materials having approximately the same effects as those of fibrous nonwoven fabrics, in the above-mentioned fastened state, the free section 22 fits and presses the front waist region 13 to the body side of the wearer without floating from the outer surface of the front waist region 13.

Figure 8:
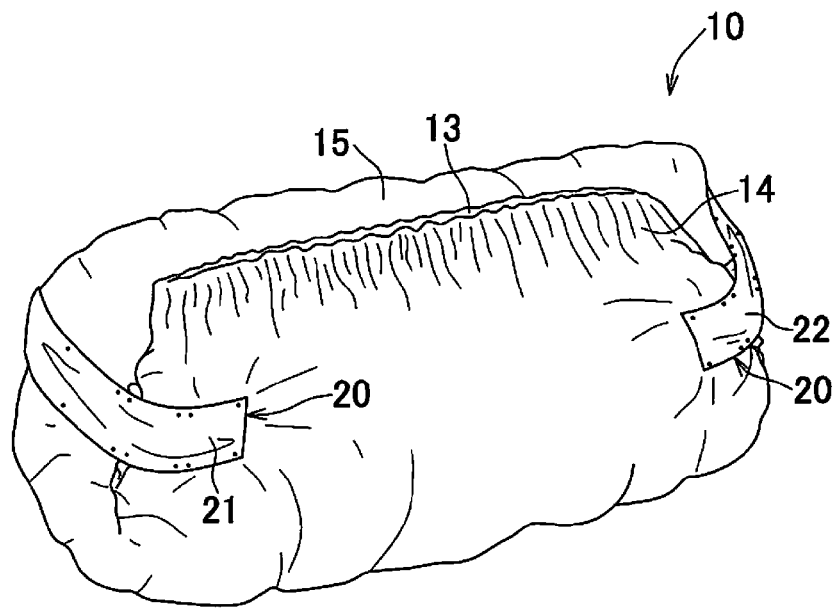
FIG. 8 is a view showing a state where the diaper is rolled up by use of the tape fasteners.

Referring to FIG. 8, this shows one example of when the used diaper 10 is disposed of. First, after use of the diaper 10, for example, the side seams of the lateral edge portions of the front waist region 13 and the rear waist region 14 are torn, and the front waist region 13 and the rear waist region 14 are spaced apart from each other, and the lateral edge portions are folded inward, and the crotch region 15 is folded in such a manner as to be rolled up toward the front waist region 13 and the rear waist region 14. Subsequently, the free section 22 of the tape fastener 20 is fastened on the outer surface of the crotch region 15 through the fastening section 68. Accordingly, a rolled-up state of the diaper 10 can be retained, whereby the diaper 10 can be hygienically disposed of without exposing or leaking the body exudates to the outside.

Figure 9:
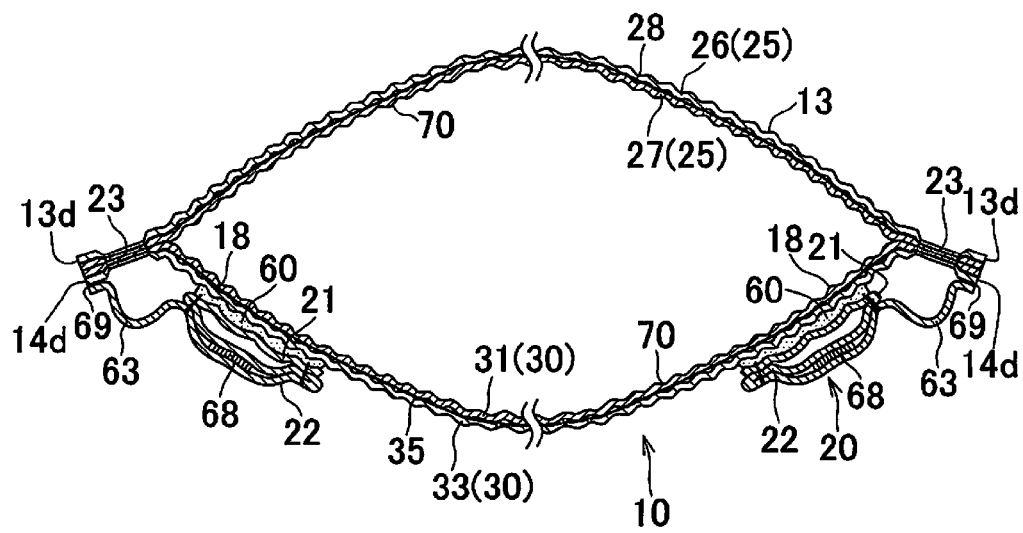
FIG. 9 is a cross-sectional view taken along line IX-IX of FIG. 1.

Referring to FIG. 9, when the diaper is worn and the tape fastener 20 is not extended, the adhesive section 69 is positioned at the adjacent area inclusive of the lateral edge 14d of the rear waist region 14, whereby the whole of the lateral edge portions are pulled backward into a state of slightly being curved backward. As the diaper 10 according to the this embodiment, when the elastic waist panel 11 and the liquid absorbent structure 12 are formed of different members, the diaper 10 has a shape in which the lateral edge portions project in the lateral direction X, so that the diaper 10 may give a neat impression when viewed from the front, owing to the lateral edge portions curved backward.

Figure 10:
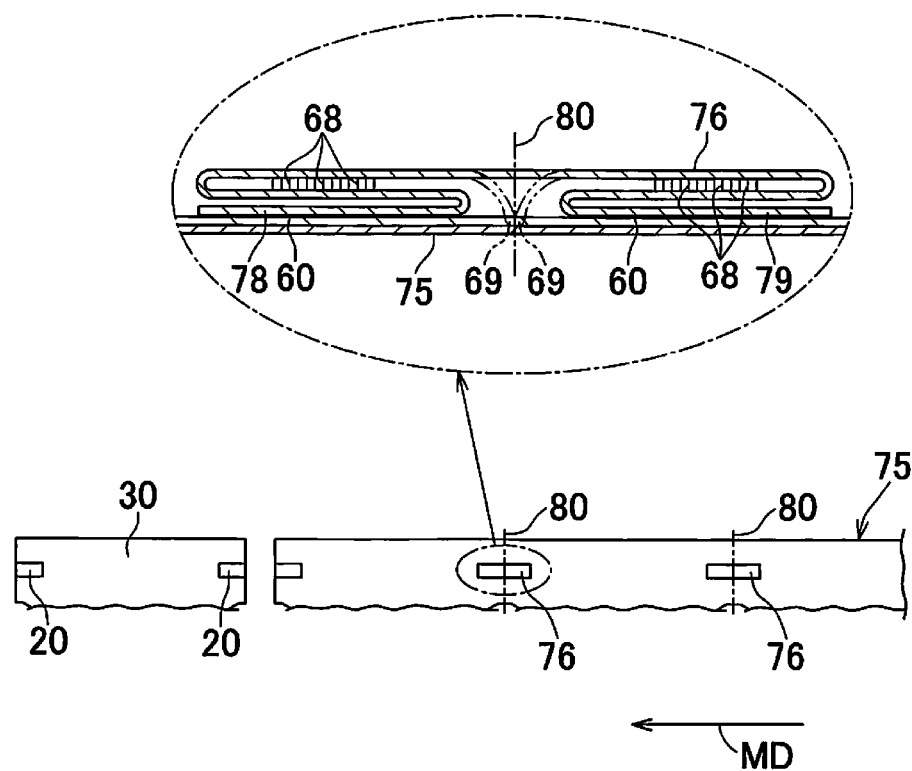
FIG. 10 is a view showing part of manufacture process of the diaper.

Referring to FIG. 10, this shows part of a manufacture process of the diaper 10. In the manufacture process of the diaper 10, a fibrous web 75, which is a base material of the rear waist sheet 30, is transferred in a mechanical direction MD. Tape base materials 76 made up of fibrous nonwoven fabrics are fixed on a first surface of the fibrous web 75, and the tape base materials 76 include the fastening section 68, whose cross section is formed in a Q shape, that is formed of hook elements such as a pair of mechanical fasteners on the inner surface. The fibrous web 75 with the tape base material 76 is cut between the fixing bilateral end portions 78, 79 of the tape base material 76 by means of a heated cutter and the like along a cut line 80 extending in the direction intersected with the mechanical direction MD, thereby obtaining a plurality of rear waist sheets 30 disposed with the tape fastener 20. In the above-mentioned process, when the fibrous web 75 and the tape base material 76 are simultaneously cut by the cutter, thermoplastic synthetic fibers forming the fibrous web 75 and the tape base material 76 is mutually thermally welded by the heat of the cutter at a cutting section, thereby forming the adhesive section 69 of the tape fastener 20. The holding end 20a of the tape fastener 20 and the lateral edge 14d of the rear waist region 14 are provided as approximately the same end surface in the thickness direction Z of the tape fastener 20 by manufacturing the diaper 10 by the above-mentioned manufacture method.

As methods for providing with the adhesive section 69, besides the method in which the above-mentioned process is used, the tape base materials 76 formed of fibrous nonwoven fabrics and the rear waist sheet 30 formed of fibrous nonwoven fabrics may be adhered with hot melt adhesives or gluing agents or may be pressurized by an emboss pin, thereby mechanically entangling fibers with one another. The fibers are mechanically entangled with one another, and the tape base materials 76 and the rear waist sheet 30 are releasably joined, so that even when the adhesive section 69 contacts the skin of the wearer, the flexible adhesive section 69 should not cause irritation, compared with a when the tape base materials 76 and the rear waist sheet 30 are joined by thermal welding means.

Second Embodiment

Figure 11:
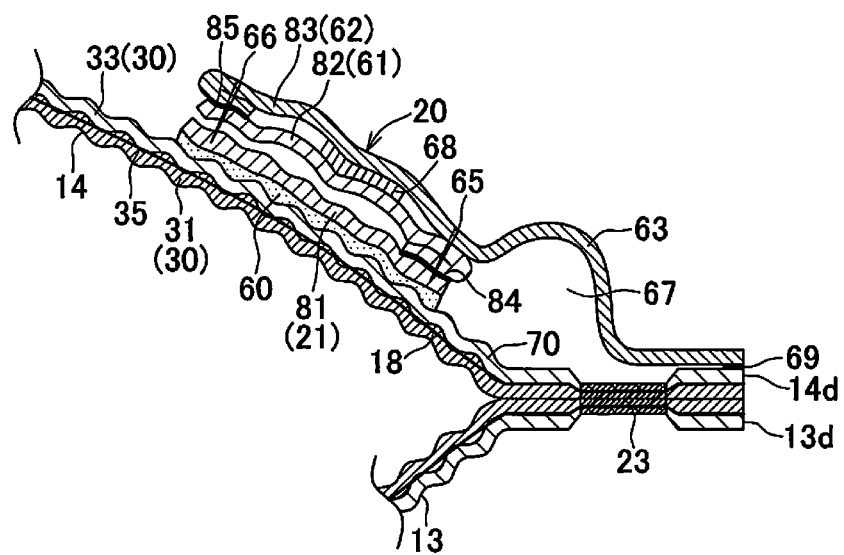
FIG. 11 is a view of the diaper similar to FIG. 6 according to a second embodiment.

Referring to FIG. 11, the tape fastener 20 according to this embodiment includes a first tape piece 81 that forms the fixed section 21, a second tape piece 82 that forms the first free section 61, and a third tape piece 83 that forms the second free section 62. The first tape piece 81 and the second tape piece 82 are joined with each other at a first join portion 84, and the second tape piece 82 and the third tape piece 83 are joined with each other at a second join portion 85. The tack portions 65, 66 are positioned at the first join portion 84 and the second join portion 85, and a state where these tape pieces 81, 82, 83 are disposed with one another is kept. These tape pieces are placed at the first join portion 84 and the second join portion 85, so that pressurizing and heat machining on the tack portions 65, 66 can be easily performed, and these tape pieces placed more firmly can be temporarily tacked with each other. Although not shown, besides this embodiment, the fixed section 21 may be formed of the first tape piece 81, and the entire free section 62 inclusive of the first free section 61 and the second free section 62 may be formed of the second tape piece 82.

Third Embodiment

Figure 12:
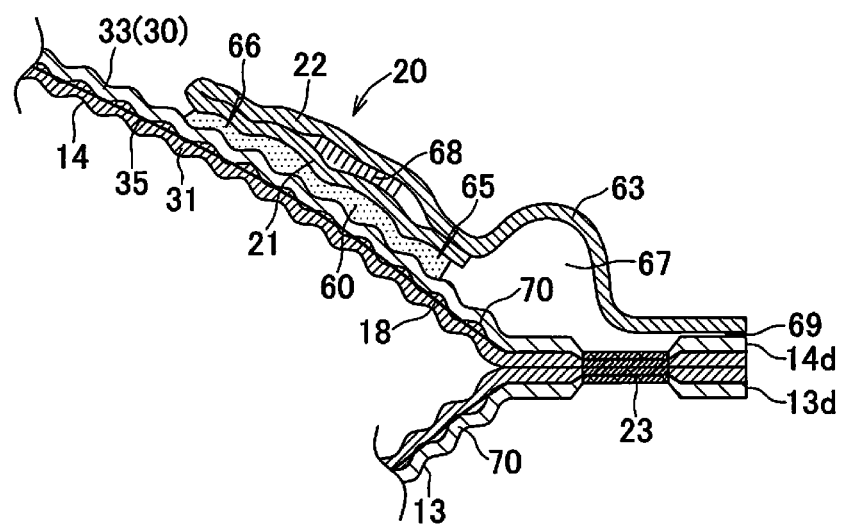
FIG. 12 is a view of the diaper similar to FIG. 6 according to a third embodiment.

Referring to FIG. 12, for the tape fasteners 20 according to this embodiment, the fixed section 21 and the free section 22 are formed of continuous tape and folded in two. Thus, even when the tape fasteners 20 are not folded multiple positions, the advantageous effects of the present invention can be achieved.

Fourth Embodiment

Figure 13:
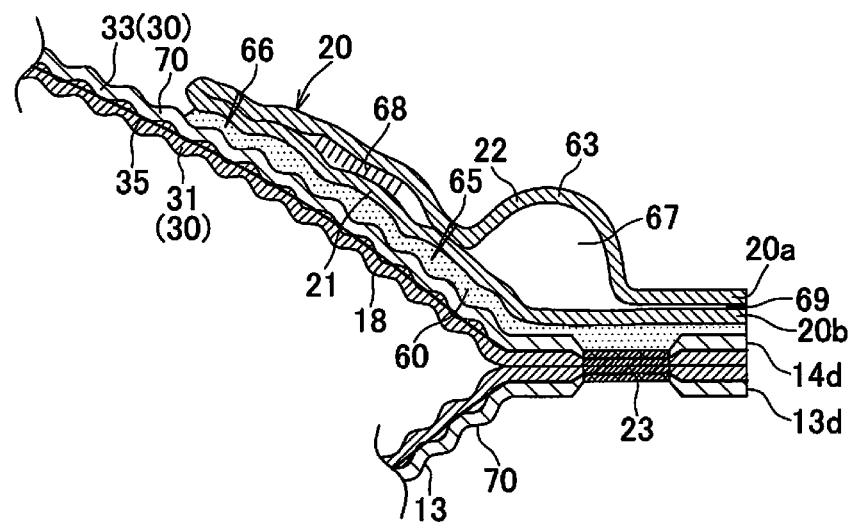
FIG. 13 is a view of the diaper similar to FIG. 6 according to a fourth embodiment.

Referring to FIG. 13, for the tape fasteners 20 according to this embodiment, the fixed section 21 and the free section 22 are formed of a continuous tape, and the holding end 20a and the fixed end 20b of the tape fastener 20 are overlapped with each other so as to approximately align to the lateral edge 14d. The holding end 20a of the tape fastener 20 is releasably fixed on the fixed end 20b through the adhesive section 69, and the holding section 63 assumes a convexly curved shape. The tape fastener 20 having the holding end 20a and the fixed end 20b are formed of fibrous nonwoven fabric containing the same fibers, so that when the holding end 20a and the fixed end 20b are joined by heating means, individual fibers can be easily fusion-bonded with each other, and temporal tacking can be performed more stably, compared with when the holding end 20a and the fixed end 20b are formed of different fibers.

Fifth Embodiment

Figure 14:
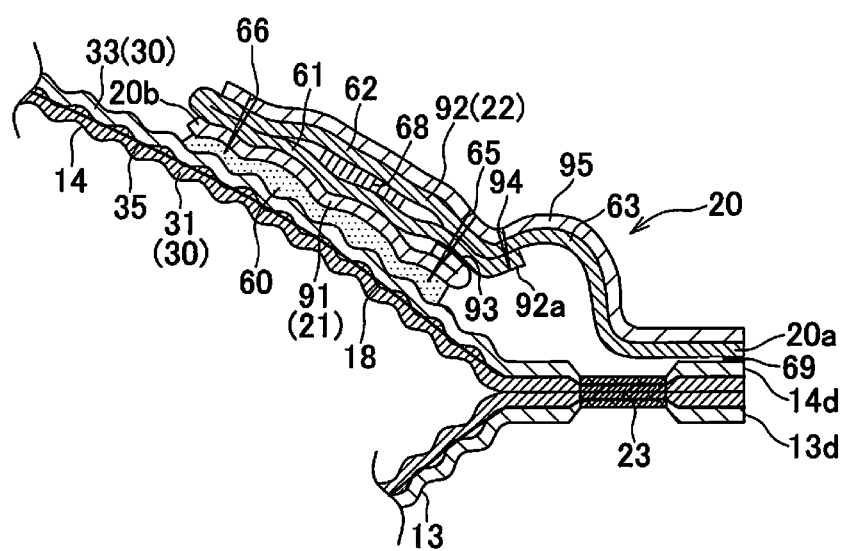
FIG. 14 is a view of the diaper similar to FIG. 6 according to a fifth embodiment.

Referring to FIG. 14, the tape fastener 20 according to this embodiment is constituted by a first tape piece 91 that forms the fixed section 21, a second tape piece 92 that is folded in two and forms the free section 22, and an auxiliary sheet 95 placed on the second tape piece 92 at the second free section 62 of the free section 22. One end of the first tape piece 91 is folded, and the first tape piece 91 is fixed with the second tape piece 92 at the fold through a join portion 93. The second tape piece 92 includes a first end 92a adjacent to the join portion 93 and a second end that forms the holding end 20a of the tape fastener 20. In the above-mentioned placed state, the fixed section 21 and the free section 22 are temporarily tacked by the tack portions 65 at the join portion 93, the tack portion 66 adjacent to the fold of the second tape piece 92, and a tack portion 94 at the first end 92a of the second tape piece 92.

The first free section 61 is formed of one tape and has flexibility and relatively low stiffness, so that a plurality of creases are generated by the contraction of the rear waist region 14, and the holding section 63 is stably convexly curved. In contrast, when the stiffness of the second free section 62 inclusive of the fastening section 68 is relatively low, the holding section 63 might be torn off or be hard to be held during the operation of the tape fastener 20. For the tape fastener 20 according to this embodiment, the auxiliary sheet 95 as a different member is placed on the second free section 62, so that the stiffness is relatively high, and there is no likelihood that the holding section 63 might be torn off during the operation of the tape fastener 20 even when the stiffness of the tape that forms the tape fastener 20 is relatively low.

Besides the materials described in the description, various known materials, which are normally used in the field of this sort, can be used for each constitution member constituting the diaper without restriction, except that materials are specifically limited. Also, the diaper may be such that the front waist region, the rear waist region 14, and the crotch region is continuously formed. For the description and claims of the present invention, the terms "first", "second", and "third" are merely used to distinguish similar elements and positions.

The above-mentioned disclosure of the present invention may be arranged in at least the following features.

The pull-on wearing article has a longitudinal direction and a lateral direction orthogonal to the longitudinal direction, a non-skin facing surface, and a skin facing surface opposed to the non-skin facing surface, and includes the first waist region, that is one of front waist regions, the second waist region that is a remainder of the rear and front waist regions, and the crotch region between the first and second waist regions, wherein lateral edge portions extending in the longitudinal direction are joined with each other in the first and second waist regions, and tape fasteners are mounted on the non-skin facing surface in the lateral region of the first waist region. At least the first waist region of the first and second waist regions is elastically stretchable in the lateral direction. The tape fastener includes the fixed section fixed to the lateral region of the first waist region, and the free section including the fastening section that is releasably fastened to the non-skin facing surface in the second waist region, and the holding section extending from the fastening section outward in the lateral direction and the holding end, and the holding end is releasably fixed to the non-skin facing surface in the lateral region of the first waist region. The region between the fastening section of the first waist region and the holding end contracts, whereby the holding section assumes a convexly curved shape.

The present invention disclosed in the above paragraph 0044 may include at least the following embodiments. The embodiments, which may be taken in isolation form or in combination with one another.

(1) The fixed section and the free section are temporarily tacked by a tack portion positioned outward in the lateral direction with respect to the fastening section, and the holding section is positioned between the tack portion and the holding end.

(2) The tape fasteners are formed of fibrous nonwoven fabrics.

(3) The fastening section includes hook elements of mechanical fasteners.

(4) The tape fasteners and the non-skin facing surface in the lateral region of the first waist region are formed of fibrous nonwoven fabrics that contain thermoplastic synthetic fibers, and the holding end's adjacent areas, which include the holding end, are releasably joined by one of welding fibers and mechanically entangling the fibers with one another.

(5) Facets of the holding end and an edge of the lateral region of the first waist region approximately are aligned.

(6) The tack portion is created at overlapped portion of the tape fastener by one of pressurization treatment and pressurization heating treatment.

(7) The free section is temporarily tacked to the fixed section in a folded state and includes a second free section contiguously disposed with the fixed section and opposed in a thickness direction of the tape fasteners, and a first free section contiguously disposed with the second free section and opposed in the thickness direction, and wherein the fixed section and the first and second free sections are temporarily tacked by the pair of tack portions configured to space apart from one another in the lateral direction and penetrated the fixed section and the first and second free section, and the fastening section is positioned on an inner surface of the first free section positioned between the pair of tack portions.

(8) The tape fastener includes a first tape piece configured to form the fixed section and a second tape piece configured to form the free section, and an auxiliary sheet formed of fibrous nonwoven fabrics is placed on the second free section of the free section.

(9) A space opened in the longitudinal direction is formed between the holding section having a convexly curved shape and the lateral region of the first waist region opposed to the holding section.

REFERENCE SIGNS LIST 10 pull-on wearing article (disposable diaper)
13 front waist region (first or second waist region)
14 rear waist region (first or second waist region)
15 crotch region
18 lateral region
20 tape fastener
20a first end (holding end)
20b second end (fixed end)
21 fixed section
22 free section
61 first free section
62 second free section
63 holding section
65, 66 tack portion
67 space
68 fastening section
91 first tape piece
92 second tape piece
94 auxiliary sheet

The invention claimed is:
1. A pull-on wearing article, comprising:
a longitudinal direction,
a lateral direction,
a non-skin facing surface,
a skin facing surface opposed to the non-skin facing surface, a first waist region that is one of rear and front waist regions, a second waist region that is a remainder of the rear and front waist regions, a crotch region between the first and second waist regions, and a tape fastener mounted on the non-skin facing surface in a lateral region of the first waist region, wherein lateral edge portions of the first and second waist regions are joined with each other, at least the first waist region of the first and second waist regions is elastically stretchable in the lateral direction, the tape fastener includes a fixed section fixed on the lateral region of the first waist region, and a free section having a fastening section that is releasably fastened to the non-skin facing surface in the second waist region, a holding section extending from the fastening section, and a holding end, the holding section is between the fastening section and the holding end in the lateral direction, the holding end of the tape fastener is releasably fixed onto the non-skin facing surface in the lateral region of the first waist region through an adhesive section inclusive of a lateral edge of the lateral region of the first waist region, in a state where the holding end of the tape fastener is releasably fixed onto the non-skin facing surface in the lateral region of the first waist region, the holding end of the tape fastener does not extend outwardly beyond the lateral edge of the lateral region of the first waist region, and a region of the first waist region between the fastening section and the holding end is contractible in the lateral direction to cause the holding section to form a convexly curved shape.

2. The wearing article according to claim 1, wherein the fixed section and the free section are temporarily tacked by a tack portion positioned on an outer side in the lateral direction with respect to the fastening section, and the holding section is positioned between the tack portion and the holding end in the lateral direction.

3. The wearing article according to claim 1, wherein the tape fastener is formed of fibrous nonwoven fabrics.

4. The wearing article according to claim 1, wherein the fastening section includes hook elements of mechanical fasteners.

5. The wearing article according to claim 1, wherein the tape fastener and the non-skin facing surface in the lateral region of the first waist region are formed of fibrous nonwoven fabrics that include thermoplastic synthetic fibers, and the holding end of the tape fastener is releasably joined to the non-skin facing surface in the lateral region of the first waist region with fusible fibers or by mechanical entanglement of fibers of the tape fastener with fibers of the non-skin facing surface in the lateral region of the first waist region.

6. The wearing article according to claim 2, wherein the tack portion is at an overlapped portion of the tape fastener where the free section overlaps the fixed section.

7. The wearing article according to claim 1, wherein the free section is temporarily tacked to the fixed section in a folded state of the free section, and the free section includes a first free section contiguously extending from the fixed section and opposed to the fixed section in a thickness direction of the tape fastener, and a second free section contiguously extending from the first free section and opposed to the first free section in the thickness direction, the tape fastener includes a pair of tack portions spaced apart from each other in the lateral direction and extending through the fixed section and the first and second free sections in the thickness direction of the tape fastener, the fixed section and the first and second free sections are temporarily tacked by the pair of tack portions, and the fastening section is positioned on an inner surface of the second free section positioned between the pair of tack portions.

8. The wearing article according to claim 1, wherein the tape fastener includes a first tape piece defining the fixed section and a second tape piece defining the free section, and an auxiliary sheet formed of fibrous nonwoven fabrics and placed on the second free section of the free section.

9. The wearing article according to claim 1, wherein a space opened and extending in the longitudinal direction is formed between the holding section having the convexly curved shape and the lateral region of the first waist region opposed to the holding section, and said convexly curved shape of the holding section is configured to be convex away from a wearer's skin.

10. The wearing article according to claim 1, wherein the holding section is configured to be picked and pulled up by a user and is free of direct attachment to the non-skin contacting surface in the lateral region of the first waist region and to the fixed section.

11. The wearing article according to claim 10, wherein the holding section and the holding end of the tape fastener are formed of a single sheet.

12. The wearing article according to claim 11, wherein the holding end of the tape fastener is directly releasably fixed onto the non-skin facing surface in the lateral region of the first waist region through the adhesive section inclusive of the lateral edge of the lateral region of the first waist region.

13. The wearing article according to claim 10, wherein the single sheet forming the holding section and the holding end is arranged on an outer side of the non-skin facing surface in a thickness direction of the wearing article.

14. The wearing article according to claim 1, wherein the adhesive section, the lateral edge of the lateral region of the first waist region, and the holding end of the tape fastener are flush with each other.

15. The wearing article according to claim 1, wherein the tape fastener is directly mounted on the non-skin facing surface in the lateral region of the first waist region at (a) a join section between the fixed section and the non-skin facing surface and (b) the adhesive section between the holding end and the non-skin facing surface.

16. The wearing article according to claim 15, wherein the join section is spaced away from the adhesive section in the lateral direction of the wearing article.

* * * * *